US009352851B2

(12) United States Patent
Tudor et al.

(10) Patent No.: US 9,352,851 B2
(45) Date of Patent: May 31, 2016

(54) NONINTRUSIVE INSPECTION METHOD AND SYSTEM OF AIRCRAFTS

(71) Applicant: MB TELECOM LTD., Otopeni, Ilfov (RO)

(72) Inventors: Mircea Tudor, Bucuresti (RO); Adrian Bîzgan, Bucuresti (RO); Constantin Sima, Bucuresti (RO); Ionel Chirita, Bucuresti (RO); Andrei Iacobita, Bucuresti (RO); Emilian Mieilica, Bucuresti (RO); Adrian Osvat, Bucuresti (RO); Cristian Prioteasa, Jud. Olt (RO); Ovidiu Popovici, Bucuresti (RO); Anda Dobrescu, Bucuresti (RO); Doru Munteanu, Bucuresti (RO); Emil Studineanu, Bucuresti (RO); Nicusor Birsan, Jud. Prahova (RO)

( * ) Notice: Subject to any disclaimer, the term of this patent is extended or adjusted under 35 U.S.C. 154(b) by 0 days.

(21) Appl. No.: 14/408,743

(22) PCT Filed: Dec. 6, 2012

(86) PCT No.: PCT/RO2012/000030
§ 371 (c)(1),
(2) Date: Dec. 17, 2014

(87) PCT Pub. No.: WO2014/081327
PCT Pub. Date: May 30, 2014

(65) Prior Publication Data
US 2015/0197349 A1    Jul. 16, 2015

(30) Foreign Application Priority Data
Jun. 18, 2012  (RO) .............................. a2012 00443

(51) Int. Cl.
*G01N 23/00*     (2006.01)
*G01V 5/00*      (2006.01)
*B64F 5/00*      (2006.01)

(52) U.S. Cl.
CPC .............. *B64F 5/0045* (2013.01); *G01N 23/00* (2013.01); *G01V 5/0008* (2013.01); *G01N 2223/631* (2013.01)

(58) Field of Classification Search
CPC . G01V 5/0016; G01V 5/0083; G01V 5/0008; G01V 5/0091; G01V 5/0025; G01V 5/0066; B64F 5/0045; G01N 23/00; G01N 23/203; G01N 23/04; G01N 23/05; G01N 23/083; G01N 2223/631; H05G 1/02; G03B 42/028
See application file for complete search history.

(56) References Cited

U.S. PATENT DOCUMENTS 6,378,387 B1 * 4/2002 Froom .................... 73/865.8
7,732,772 B1    6/2010 Koltick et al.
(Continued)

FOREIGN PATENT DOCUMENTS

WO      2006036076 A1    4/2006

OTHER PUBLICATIONS
International Search Report for PCT/RO2012/000030 dated Jun. 19, 2014.

*Primary Examiner* — Rodney Butler
(74) *Attorney, Agent, or Firm* — Dennemeyer & Associates, LLC

(57) ABSTRACT

The nonintrusive control method consists in using a tugging device attached to the aircraft's landing gear which is towing the aircraft over a detector line, detector line fixed onto the runway under a penetrating radiation source held by a telescopic boom fixed on a mobile scanning unit. The aircraft is towed with constant speed and electronically controlled in a secured and delimited perimeter. The system consists of a mobile scanning unit (MSU), controlled remotely by a towable mobile control center positioned outside an exclusion area. The MSU consists of a telescopic boom holding on its extremity a penetrating radiation source and a detector line fixed onto the runway and a tugging device, which attaches to the aircraft's undercarriage.

7 Claims, 3 Drawing Sheets

(56) References Cited

U.S. PATENT DOCUMENTS

Figure 1:
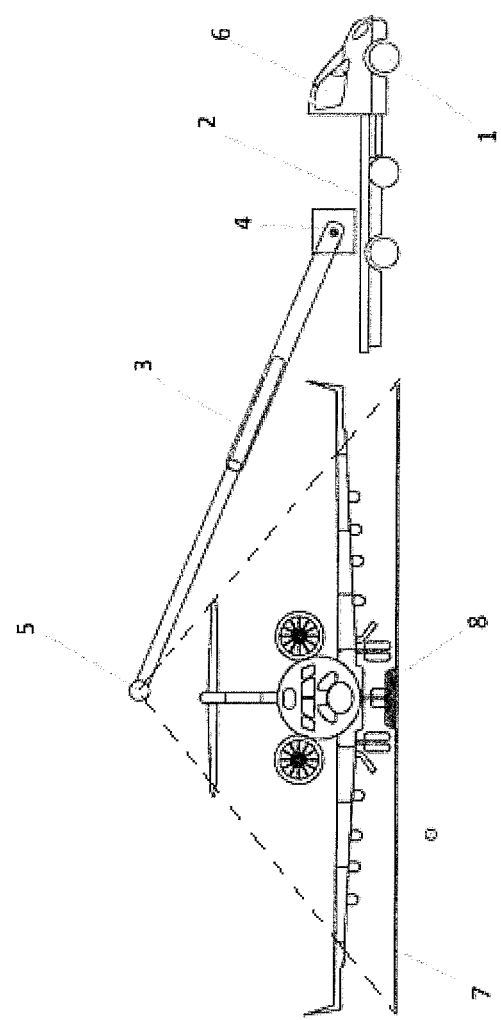

| | | | |
|---|---|---|---|
| 2003/0091145 A1* | 5/2003 | Mohr et al. | 378/58 |
| 2003/0147493 A1* | 8/2003 | Bueno et al. | 378/57 |
| 2004/0258198 A1* | 12/2004 | Carver et al. | 378/57 |
| 2008/0123809 A1* | 5/2008 | Tudor et al. | 378/57 |
| 2008/0205594 A1* | 8/2008 | Bjorkholm | 378/53 |
| 2011/0103548 A1* | 5/2011 | Bendahan | 378/57 |
| 2013/0261876 A1* | 10/2013 | Froom et al. | 701/29.3 |
| 2015/0134274 A1* | 5/2015 | Froom et al. | 702/39 |

* cited by examiner

NONINTRUSIVE INSPECTION METHOD AND SYSTEM OF AIRCRAFTS

The present invention consists of a method and a system for the nonintrusive inspection of aircrafts. The inspection can be achieved without direct human intervention, thus eliminating time consuming activities like actual physical control.

By using the present invention a radiographic image of the aircraft is obtained, image upon which a specifically trained operator can evaluate the quantity and the nature of the objects and the cargo loaded onto the scanned aircraft. By analyzing the radiographed images is expected to detect contraband, illegal transports of forbidden or undeclared products (like drugs, explosives and weapons), in strategically designated areas which require a high level of security like airports.

The nonintrusive inspection system implies the irradiation of a row of detectors linearly placed on the airport runway, in front of a penetrating radiation beam, system which is in a relative motion to the scanned object. The electrical signals emitted by the detectors are processed analogically/digitally with the purpose of generating, line by line, a radiography which will be displayed on a PC screen. The signal intake and processing generated from a large number of detectors, usually hundreds, implies complex electronic blocks and a network of wires with a large number of parallel connections between the boom and the subsystems that generate a radiographic image.

Currently the global market offers several scanning systems which include, in various combinations, the aircraft scanning technologies presented above. Such example is the system described by the U.S. Pat. No. 5,014,293/May 10, 1991 patent, a system which is heavy and consists of an assembly on which a "C" shaped boom slides, assembly which has on one side the detector area and on the opposite side a radiation source. The disadvantage of this system consists of the fact that the detector boom has a fixed length, impossible to adjust according to the scanned aircrafts' dimension. Another inspection system described by the U.S. Pat. No. 6,466,643/Oct. 15, 2002 patent proposes a solution in which the radiation source is placed inside the fuselage and the detectors are placed on the exterior of the fuselage thus resulting in a time consuming scanning process because the source needs to be relocated every time a scanning process takes place.

The technical issue handled by the present invention is the development of a nonintrusive inspection method for aircrafts, with a high scanning capacity, by obtaining a complete radiography of the aircraft, while said aircraft is being towed by a tugging device located on the runway, through the scanning portal and the realization of a system that implements the above method, said system being easily and rapidly transported in areas which demand the assurance of a high security rate.

The nonintrusive control method, according to the invention, eliminates the disadvantages mentioned above by the fact that the currently inspected enters the scanning area, area defined by the exclusion zone protection subsystem. The said aircraft is placed into the exclusion area and then it is towed by a tugging device with constant speed, passing through a scanning structure, referred to as portal from this point on. Said portal has a radiation detector line placed onto the runway, and in the opposite direction, above the scanned aircraft, a penetrating radiation source. The aircraft is towed through the portal with a recommended speed, according to the aircraft's type and its' cargo load, said speed being calculated by a speed measurement system placed on the mobile unit. The approach of the aircraft with recommended speed towards the portal generates the activation of the radiation source. The scanning process stops automatically in the following cases: when the aircraft has completely passed over the detector area located on the runway, when intruders breach the exclusion area, when a sensor transmits a message, signaling that the aircraft is out of its' predefined trajectory on passing over the detector line and when the aircrafts' speed fluctuates outside the predefined limits, said limits which the system cannot manage. The scanning process can be stopped manually by the operator at any given time. During the scanning process, the resulting image of the inspected aircraft is displayed on the operator's screen simultaneous and synchronized with the aircraft's movement. At the end of the scanning phase, the automatic perimeter protection system of the exclusion area is deactivated right after the radiation source is stopped.

The radiation source used in the nonintrusive inspection system, according to the invention, can be a natural source with radioactive material (such as Co60), an X-Ray generator or a linear accelerator. When using a natural source, the material choice is decided according to the level of penetration wanted and the dimensions of the exclusion area available in the scanning location. The capsule that contains radioactive material is sealed in a container which has sufficient shielding, so that the level of radiation on the exterior surface of the container is within the limits established by the International Atomic Energy Agency (IAEA). Using this type of radiation source (Co60), penetration can reach up to 230 mm in aluminum.

The system that implements the scanning method presented above consists of a mobile scanning unit (MSU) installed on a chassis, said chassis which has a telescopic boom mounted, said boom which holds at its extremity the penetrating radiation source. In "transport mode" the boom is folded in order to insure a minimum overall dimension that allows the enrollment of the vehicle in the authorized dimensions of public road transportation. In "scanning mode", the boom extends, thus describing a variable angle with the chassis, said dimension of the angle which depends on the scanned aircraft's total height.

The boom's motion is executed automatically by hydraulic cylinders commanded by a PLC through some hydraulic proportional valves. The mobile scanning unit also consists of a position monitoring subsystem. The scanning system also includes a mobile control center (MCC), which is positioned outside the exclusion area and its' purpose is to remotely manage all the processes involved in the nonintrusive inspection. Inside the mobile control center there is an acquisition, processing, storage and display subsystem of the radiographed image. The scanning system also includes a perimeter protection system.

The mobile scanning unit is equipped with an extra chassis, said chassis which holds the boom that supports the radiation source in a two degree rotary joint, said boom which has a telescopic construction of several segments depending on the dimensions of the scanned aircraft. The detector area is placed on the airports' runway and is mounted on an easy to maneuver metallic stand by the operator of the system. In transport mode, the telescopic boom is folded along the chassis, the detector line and the tugging device are loaded onto the chassis, more exactly on the supplementary chassis. The system is converting into scanning mode following this sequence:

The detector line is unloaded from the chassis and is fixed on the runway by the operator, in such a position so that it forms a 180 degree angle with the chassis and at a distance equal to the telescopic boom length;

The tugging device is unloaded from the chassis and placed by the exclusion area's entrance, next to the detector line, with the purpose to be attached to the aircraft to be scanned;

The telescopic boom performs a rotating motion with respect to the chassis, forming a variable degree angle with the chassis' plan, said angle which is calculated based on the scanned aircraft's dimensions;

The telescopic boom performs an extension motion, up to a predefined length, depending on the scanning site's characteristics;

The telescopic boom performs a rotating motion with respect to the transversal axle of the chassis, so that the radiation source, said source which is located at the boom's extremity, is aligned vertically with the detector line;

By using the present invention, there are consistent advantages such as:

A high scanning capacity of aircrafts in a short period of time (up to 20 aircrafts per hour);

A complete inspection of the aircraft, including the cockpit, the body of the aircraft and the aircraft's cargo bay;

The professional radiation risk of the operators is eliminated as well as the accidental radiation risk of the possible intruders from the exclusion area;

The necessary number of operators per shift is only 1 person;

A high system mobility, flexibility and handling;

A high level of automation;

Preservation of the dynamic performances of the chassis, in transport mode;

High productivity rate, by scanning up to 20 aircrafts per hour by automating processes and reducing dead times generated by the computerized management of the processes.

Figure 2:
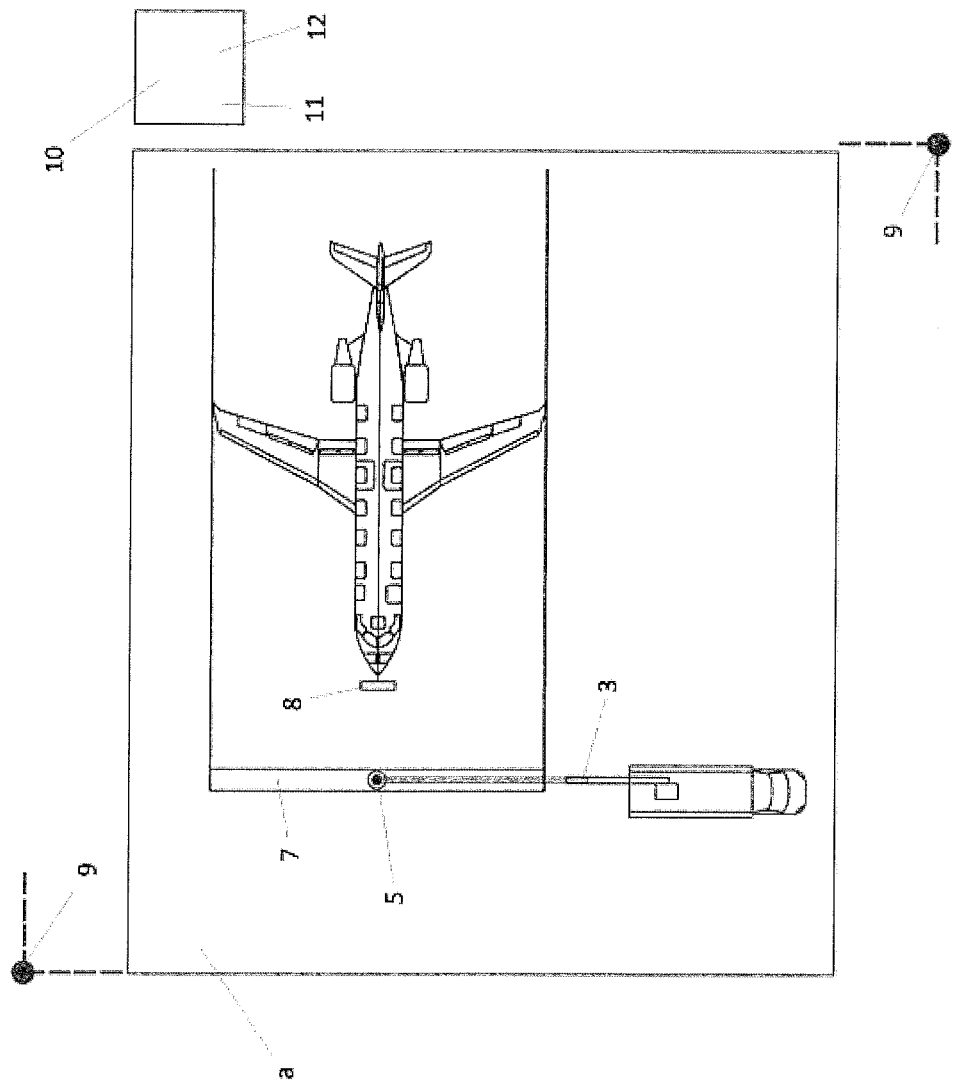
Figure 3:
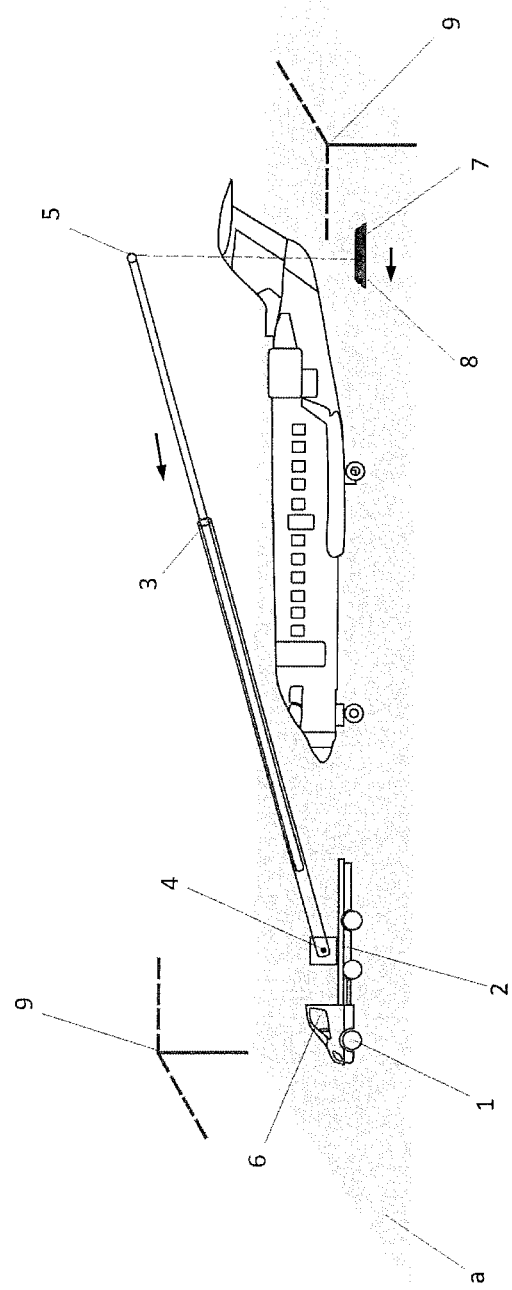

The nonintrusive control method, according to the invention, when the mobile scanning unit is stationary, comprises of the following steps:

The detector line is fixed on the airport's runway;

The tugging device is unloaded from the chassis and attached to the aircrafts' landing gear;

The aircraft is towed in the exclusion area and awaits scanning;

The operator located in the mobile control center initiates the scanning process by remotely transmitting a command to the mobile scanning unit, said unit used as a portal structure;

When the aircraft approaches the portal area, the penetrating radiation source is activated and the said aircraft is towed with a recommended speed so that it is scanned;

The scanning process automatically stops in the following cases:

when the aircraft has completely passed over the detector area located on the runway;

when intruders breach the exclusion area;

when a sensor transmits a message, signaling that the aircraft is out of its' predefined trajectory when passing over the detector line;

when the aircrafts' speed fluctuates outside the predefined limits, said limits which the system cannot manage;

The resulted image of the scanned aircraft is displayed on the operator's screen from the mobile control center;

A folder with a unique ID is created and archived, said folder which contains the scanned image and the real image of the aircraft;

Further, an example of implementing of the invention is presented in connection with the figures from 1 to 3 that describe:

FIG. 1: (front view of the aircraft): view of the nonintrusive inspection system in scanning mode;

FIG. 2: (side view of the aircraft): view of the nonintrusive inspection system in scanning mode, in another implementation variant;

FIG. 3: perspective view of the nonintrusive inspection system, according to the invention, placed within the exclusion area;

The nonintrusive inspection system, according to the invention, is a mobile nonintrusive scanning assembly, installed on a vehicle chassis 1 with low total weigh, onto there is a supplementary chassis, referred to from this point on as a superstructure 2 which has a telescopic boom 3 mounted in a two degree joint 4, said joint which holds at its extremity the penetrating radiation source 5. The telescopic boom 3 is made out of steel and light metals and folds from the direction of the driver's cabin 6 towards the scanned aircraft.

The detector line 7 has a modular form and will be unloaded from the chassis 1 on separate modules and will be assembled and fixed on the runway, inside the exclusion area a; the tugging device 8 is also unloaded from the chassis and prepared to be attached to the aircraft's landing gear, so that it can tow the said aircraft through the scanning portal;

Because the scanning area of the aircrafts has to be actively protected against the accidental radiation of the possible intruders, a perimeter protection subsystem 9 has been foreseen that determines a rectangular exclusion zone a.

A computer management subsystem 10 commands and controls remotely all the subsystems of the whole assembly: direction, engine speed, and the position of the tugging device in the exclusion area, as well as the other connected peripherals according to the invention, communicating with them through a wireless LAN.

All the physical components of the computer management subsystem 10, as well as the operator's workstation are installed in a mobile control center 11 which during transport is towed by the chassis 1, and during the scanning process is located outside the exclusion area a.

The mobile scanning unit, according to the invention, has two physical presentation modes: scanning mode and transport mode. Conversion from one mode to another is realized by operating hydraulic cylinders, said cylinders that reconfigure the position of the telescopic boom 3.

In transport mode, the telescopic boom 3 is closed and folded along the chassis 1 in order to insure compliance with the legal dimensional limits of transport on public roads and to also distribute a good weight repartition on every wheel. The scanning systems' components: the detector line 7 and the tugging device 8 are loaded onto the chassis 1.

In scanning mode, the detector line 7 is placed onto the runway, and the tugging device 8 is attached to the landing gear of the aircraft that waits scanning. The telescopic boom 3 executes a rotating motion starting from the driver's cabin, forming a variable dimension angle with the chassis' plan 1, said angle which is determined using the scanned aircraft's total dimensions, said boom then executes an extension motion to a predefined length and finally executes a rotating motion from the transversal axle of the chassis 1, so that the radiation source which is located at the boom's extremity, aligns with the detector line. After the system has been installed, the scanning procedure can start by initiating a command to the tugging device 8 which is attached to the landing gear of the aircraft, said aircraft which is towed through the radiation portal, said portal consisting of the detector line 7 which is placed onto the runway, and of the penetrating radiation source 5, said source which is located at the extremity of the telescopic boom, said boom fixed on the mobile scanning unit; the scanning process can be automatically stopped when the aircraft has completely passed over the detector area located on the runway, when intruders breach the exclusion area, when a sensor transmits a message, signaling that the aircraft is out of its' predefined trajectory on passing over the detector line and when the aircrafts' speed fluctuates outside the predefined limits, said limits which the system cannot manage; during this phase the resulting image of the inspected aircraft is displayed on the operator's screen and a folder with a unique ID is created and archived, said folder which contains the scanned image of the aircraft and a photographic image of the aircraft; when the scanning phase is completed, the radiation source 5 is automatically stopped, the exclusion area a perimeter protection subsystem is deactivated, the tugging device 8 detaches from the aircraft, after which the said aircraft can exit the exclusion area a, and the scanning cycle can be resumed.

In another implementing variant, the mobile scanning unit is placed in front of the aircraft, the telescopic boom 3 is extended along the aircraft's length and the detector line 7, which has a certain length so as to be framed by the aircraft's landing gear, is towed by the tugging device 8 from the aircraft's tail towards the aircraft's nose, synchronized and simultaneously with the retraction motion of the telescopic boom, thus being obtained a longitudinal radiographed image of the aircraft's body.

The mobile control center 11 is placed outside the exclusion area a, zone which is delimited by the perimeter protection subsystem 9.

The chassis 1 has to be homologated according to the international standards in force, for transport on public roads without a special authorization. The chassis 1 is provided with a supplementary steel chassis, the superstructure 2, which holds all the components of the mobile scanning unit: the annexes of the hydraulic system: the oil tank, distributors, safety and control circuits, electric and electronic circuit cabinets. Some of these parts are not marked on the drawings as they are well known and unclaimed components.

The penetrating radiation source 5 is fixed at the superior end of the telescopic boom 3, such that the beam of radiation is collimated on the detectors line 7 situated on the runway, with the purpose of transforming the perceived penetrating radiation into electrical signals which are further processed and transformed in radiographic images of the scanned aircraft. Therefore, if an X-Ray generator will be used, then hybrid detectors with scintillation crystals and photodiodes or monolithic detectors with load coupled circuits will be used; in the case of a gamma radiation source, hybrid detectors with scintillation crystals coupled with photomultiplier tubes will be used. The detector alignment can be done, depending on the chosen radiation source and the construction of the detectors on one row, two rows or in a variable dimension matrix.

The perimeter protection subsystem 9 of the exclusion area a is an active radiological protection subsystem which applies directly to the penetrant radiation source 5, so that the source 5 is automatically shut down in case intruders breach the exclusion area a, in order to protect them against accidental radiation leaks. The active sensors that compose the perimeter protection subsystem are placed in pairs, at the extremities of the exclusion area a, oriented at 90 degrees one from the other, creating a virtual curtain which defines a rectangular area which' dimensions depend on the current regulations of each country where the scanning process takes place. These sensors are permanently connected, through radio, to the mobile control center 11, towards which they send an alarm signal in case intruders breach the area, said signal that shuts down automatically the source 5 and activates a text, vocal and graphical message on the graphical interface of the operator's software application, indicating which side has been breached. The subsystem was designed to function in difficult meteorological conditions like rain, snow, wind, extreme temperatures, etc. The perimeter protection is deactivated so that it allows the entrance/exit in and from the exclusion area.

The mobile control center 11 operates all the components and the peripherals that compose the mobile scanning system, insuring the automation of the processes.

What is claimed:

1. A nonintrusive inspection system comprising: a scanning unit installed on a vehicle chassis, a portal in the shape of a triangle through which an aircraft is being towed, a remote controlled tugging device for aircraft towing, a superstructure mounted on said chassis, a telescopic boom mounted in a two degree joint which holds on its superior extremity a penetrating radiation source, a modular detector line placed on the runway in a fixed position, an exclusion area protection subsystem bounding an exclusion area, a mobile control center placed outside said exclusion area, and an acquisition, processing, storage and image display system, wherein said aircraft is towed through said portal over the detector line, being entirely scanned by said system.

2. A nonintrusive inspection system according to claim 1, wherein the modules of the detector line are loaded on the chassis in transport mode, and fixed on the airport's runway or ground in scanning mode.

3. A nonintrusive inspection system according to claim 1, wherein the tugging device is loaded on the chassis in transport mode, and is attached to the aircraft's front landing gear in scanning mode, thus towing the aircraft through the radiation portal.

4. A nonintrusive inspection method for use with the aircraft scanning using radiation, described in claim 1, comprising the following stages:

Placing the aircraft to be scanned inside an exclusion area;

Activating a perimeter protection of an exclusion area;

Attaching the aircraft awaiting to be scanned, by its front landing gear, to a remote operated tugging device;

Initiating the scanning process by remote transmission of a command from an operator in a mobile control center, placed outside of the exclusion area, to a scanning unit, for activating a penetrating radiation source and to the remote operated tugging device attached to the front landing gear of the aircraft for starting the aircraft's translation through the scanning portal;

Translating the towed aircraft through a radiation portal, said portal in the shape of a triangle consisting of a horizontal detector line which is placed onto the runway, as base of the triangle, and of a penetrating radiation source, as top vertex of the triangle, said source being located at a certain height on the plane perpendicular on the detector line, at the extremity of a telescopic boom, said boom being attached to the scanning unit with variable angle positioning;

Automatically stopping the scanning process when the aircraft has completely passed over the detector line located on the runway, when intruders breach the exclusion area, when a sensor transmits a message signaling that the aircraft is out of its predefined trajectory, and when the aircraft' speed fluctuates outside the predefined limits, said limits which the system cannot safely manage;

Displaying the radiographed image generated during scanning process on an operator's screen;

Creating a file containing a scanned image and a photographed image of the aircraft, and storing it under a unique identity;

Shutting-down the radiation source after the scanning process is completed, the perimeter protection subsystem being deactivated, the remote tugging device being detached from the aircraft's front landing gear;

The aircraft leaves the exclusion area and the scanning cycle can be resumed.

5. A nonintrusive inspection method for use with the aircraft scanning using radiation, described in claim 2, comprising the following stages:

Placing the aircraft to be scanned inside an exclusion area;

Activating a perimeter protection of an exclusion area;

Attaching the aircraft awaiting to be scanned, by its front landing gear, to a remote operated tugging device;

Initiating the scanning process by remote transmission of a command from an operator in a mobile control center, placed outside of the exclusion area, to a scanning unit, for activating a penetrating radiation source and to the remote operated tugging device attached to the front landing gear of the aircraft for starting the aircraft's translation through the scanning portal;

Translating the towed aircraft through a radiation portal, said portal in the shape of a triangle consisting of a horizontal detector line which is placed onto the runway, as base of the triangle, and of a penetrating radiation source, as top vertex of the triangle, said source being located at a certain height on the plane perpendicular on the detector line, at the extremity of a telescopic boom, said boom being attached to the scanning unit with variable angle positioning;

Automatically stopping the scanning process when the aircraft has completely passed over the detector line located on the runway, when intruders breach the exclusion area, when a sensor transmits a message signaling that the aircraft is out of its predefined trajectory, and when the aircraft' speed fluctuates outside the predefined limits, said limits which the system cannot safely manage;

Displaying the radiographed image generated during scanning process on an operator's screen;

Creating a file containing a scanned image and a photographed image of the aircraft, and storing it under a unique identity;

Shutting-down the radiation source after the scanning process is completed, the perimeter protection subsystem being deactivated, the remote tugging device being detached from the aircraft's front landing gear;

The aircraft leaves the exclusion area and the scanning cycle can be resumed.

6. A nonintrusive inspection method for use with the aircraft scanning using radiation, described in claim 3, comprising the following stages:

Placing the aircraft to be scanned inside an exclusion area;

Activating a perimeter protection of an exclusion area;

Attaching the aircraft awaiting to be scanned, by its front landing gear, to a remote operated tugging device;

Initiating the scanning process by remote transmission of a command from an operator in a mobile control center, placed outside of the exclusion area, to a scanning unit, for activating a penetrating radiation source and to the remote operated tugging device attached to the front landing gear of the aircraft for starting the aircraft's translation through the scanning portal;

Translating the towed aircraft through a radiation portal, said portal in the shape of a triangle consisting of a horizontal detector line which is placed onto the runway, as base of the triangle, and of a penetrating radiation source, as top vertex of the triangle, said source being located at a certain height on the plane perpendicular on the detector line, at the extremity of a telescopic boom, said boom being attached to the scanning unit with variable angle positioning;

Automatically stopping the scanning process when the aircraft has completely passed over the detector line located on the runway, when intruders breach the exclusion area, when a sensor transmits a message signaling that the aircraft is out of its predefined trajectory, and when the aircraft' speed fluctuates outside the predefined limits, said limits which the system cannot safely manage;

Displaying the radiographed image generated during scanning process on an operator's screen;

Creating a file containing a scanned image and a photographed image of the aircraft, and storing it under a unique identity;

Shutting-down the radiation source after the scanning process is completed, the perimeter protection subsystem being deactivated, the remote tugging device being detached from the aircraft's front landing gear;

The aircraft leaves the exclusion area and the scanning cycle can be resumed.

7. A nonintrusive inspection method characterized in that, a mobile scanning unit is placed in front of an aircraft, a telescopic boom is extended along the aircraft's length bringing a penetrating radiation source above the aircraft's tail, a detector line which has a certain length in order to be framed by the aircraft's landing gear is towed by a tugging device under the aircraft's fuselage, from the aircraft's tail towards the aircraft's nose, simultaneously and synchronized with the retraction motion of the telescopic boom, so that a longitudinal radiographed image of the aircraft's fuselage is obtained, said image being displayed on an operator's screen from a mobile control center, said mobile control center being placed outside an exclusion area.

* * * * *